(12) United States Patent
Fujita

(10) Patent No.: US 7,428,052 B2
(45) Date of Patent: Sep. 23, 2008

(54) OPTICAL TOMOGRAPHIC APPARATUS

(75) Inventor: Hiroshi Fujita, Saitama (JP)

(73) Assignee: Fujinon Corporation, Saitama (JP)

( * ) Notice: Subject to any disclaimer, the term of this patent is extended or adjusted under 35 U.S.C. 154(b) by 340 days.

(21) Appl. No.: 11/296,368

(22) Filed: Dec. 8, 2005

(65) Prior Publication Data
US 2006/0146338 A1   Jul. 6, 2006

(30) Foreign Application Priority Data
Dec. 9, 2004   (JP)   ............ P.2004-356137

(51) Int. Cl.
G01B 9/02   (2006.01)
(52) U.S. Cl. .................................... 356/479
(58) Field of Classification Search ................ 356/479, 356/497, 511; 600/166, 170
See application file for complete search history.

(56) References Cited

U.S. PATENT DOCUMENTS

| | | | |
|---|---|---|---|
| 5,321,501 A | | 6/1994 | Swanson et al. |
| 5,642,196 A | * | 6/1997 | Alves et al. .................. 356/632 |
| 6,590,664 B1 | * | 7/2003 | Dogariu et al. .............. 356/479 |
| 6,822,746 B2 | * | 11/2004 | Prinzhausen et al. ........ 356/497 |
| 6,934,027 B2 | * | 8/2005 | Prinzhausen et al. ........ 356/417 |
| 6,970,253 B2 | * | 11/2005 | Lindner et al. .............. 356/511 |
| 2002/0180982 A1 | * | 12/2002 | Prinzhausen et al. ........ 356/497 |

FOREIGN PATENT DOCUMENTS

| | | |
|---|---|---|
| JP | 2003-35660 A | 2/2003 |
| JP | 2003-329577 A | 11/2003 |
| WO | WO-97/32182 A1 | 9/1997 |

OTHER PUBLICATIONS

Sato et al., Fundamentals of Optical Coherence Tomography, Optics, 2003, 32-4, 268(68)-274(74).

* cited by examiner

*Primary Examiner*—Patrick J Connolly
(74) *Attorney, Agent, or Firm*—Birch, Stewart, Kolasch & Birch, LLP

(57) ABSTRACT

An optical tomographic apparatus is provided and includes a light source portion, and an interferometer including a probe. A vicinity of a fore-end of a probe is provided with a concave mirror and a portion spaced apart from the concave mirror by a distance therebetween is provided with a semitransparent mirror and a GRIN lens successively from a fore-end side of the probe. On the other hand, the probe includes light transmitting window portions at positions different from each other by 180 degrees in a peripheral direction thereof, and a subject can be irradiated and subject light can be acquired in two directions in the peripheral direction of the probe. Thereby, there is constructed a constitution capable of acquiring information twice as much as that of a related art by one time irradiation to the subject by a comparatively simple constitution.

7 Claims, 4 Drawing Sheets

OPTICAL TOMOGRAPHIC APPARATUS

FIELD OF THE INVENTION

The present invention relates to an optical tomographic apparatus used in providing a tomographic image of a subject in a medical or industrial field or the like.

BACKGROUND OF THE INVENTION

In recent years, in a field of taking an image of a subject for medical use, industrial use or the like, particularly, in a field of an electronic endoscope, there is known an apparatus of taking a tomographic image of a subject by using a method of OCT (optical coherence tomography).

According to the tomographic apparatus by OCT, light is used as a detecting probe and therefore, there is not posed a problem that a subject is exposed to X-ray irradiation as in an X-ray imaging apparatus of a background art, and the apparatus is extremely preferable particularly when the subject is the human body. Further, a large-sized apparatus of CT, MRI or the like is not needed, the subject can simply be inspected and therefore, a burden of the subject in view of cost or a burden in view of a physical strength thereof can be alleviated and the apparatus is preferable also in this respect.

Further, according to the tomographic apparatus using OCT, by utilizing low coherence of light having a spector width in a wide band, interference wave information at respective positions in a depth direction of the subject is provided and therefore, reflected light from an inner portion of the subject can be detected by a spatial resolution of µm order, and a measurement resolution can considerably be promoted in comparison with that of the X-ray imaging apparatus of the background art.

The tomographic apparatus using OCT having a number of excellent characteristics in this way is disclosed in, for example, Optics vol.32, No.4 (2003): Manabu Sato, Naohiro Tanno. Further, there is specifically proposed a tomographic apparatus using OCT which is technically devised variously (refer to, for example, JP-A-2003-329577 or the like).

However, it is a current state that an apparatus which is satisfactory in a speed of acquiring image information with regard to a subject, an amount of information thereof or the like has not been necessarily proposed and reduced into practice and a further improvement has been desired.

SUMMARY OF THE INVENTION

The invention has been carried out in view of such a situation, and an object of an illustrative, non-limiting embodiment of the invention is to provide an optical tomographic apparatus capable of acquiring image information more than that of the related art in a short period of time by a comparatively simple constitution. Also, the invention is not required to solve the above-described problems, and an illustrative, non-limiting embodiment of the invention may solve a different problem or may not solve any problems.

An illustrative, non-limiting of an optical tomographic apparatus of the invention is characterized in comprising:
  a light source for emitting light having low coherence; and
  an interferometer for dividing light emitted from the light source in two light, irradiating a subject with one of the two light, irradiating a reference face with the other of the two light, combining reference light from the reference face and subject light from the subject so as to obtain an interference light flux, and photoelectrically converting the interference light into a signal so as to enable to output the signal, so that the optical tomographic apparatus enables to provide a tomographic image of the subject,
  wherein the interferometer comprises a probe for emitting irradiating light to the subject and receiving the subject light from the subject, and the probe comprises an irradiating light-separating portion for dividing the irradiating light to the subject in two irradiating light (first and second irradiating light), one of the two irradiating light being emitted in one side direction of the probe and the other of the two irradiating light being emitted in another side direction of the probe.

Further, it is preferred that: the probe comprises a reflecting mirror, a semitransparent mirror and an object optical system in this order from a side of a fore-end portion of the probe; a part of the irradiating light reaching the semitransparent mirror from the object optical system is reflected by the semitransparent mirror so that the probe emits the part of the irradiating light in one side direction the probe; and the other part of the irradiating light transmits through the semitransparent mirror, is reflected by the reflecting mirror to return again to the semitransparent mirror, and is reflected by the semitransparent mirror so that the probe emits the other part of the irradiating light in other side direction being a direction inverse to the one side direction.

In this case, it is preferred that the reflecting mirror is a concave mirror having a concave surface facing to the semitransparent mirror.

Further, it is preferred that the probe comprises a pivoting mechanism capable of rotating the semitransparent mirror on an optical axis of the object optical system.

Further, it is preferred that the interferometer comprises a Michelson type interferometer, and an optical length of the reference light is changed by moving a reflecting member having the reference face in an optical axis direction of the reflecting member.

Or, it is preferred that the interferometer comprises: a Michelson type interferometer; and an optical detector, and the interference light flux is guided to the optical detector by way of a spectroscopic optical system for separating the interference light.

Further, it is preferred that the reference light is provided by inputting and passing the other of the two light, into which the light emitted from the light source is divided, through light delaying means and optical phase modulating means in parallel, an interference light provided by combining the reference light and the irradiating light is photoelectrically converted, thereafter, separated by using two band pass filters having passing wavelength bands different from each other, so as to provide pieces of optical tomographic image information independently corresponding the irradiating light divided in two (i.e., to provide first and second optical image information corresponding to the first and second irradiating light, respectively).

According to an exemplary of an optical tomographic apparatus of the invention, the apparatus is constituted such that light can be irradiated to the subject and reflected light from the subject can be acquired in a radial direction relative to an axis line of the probe and in two directions different from each other and therefore, image information twice as much as that of the related art apparatus can be acquired in a short period of time by a comparatively simple constitution in comparison with that of the related art and further efficient image diagnosis can be carried out.

DETAILED DESCRIPTION OF THE INVENTION

An explanation will be given of an optical tomographic apparatus according to an exemplary embodiment of the invention in reference to the drawings as follows.

Figure 1:
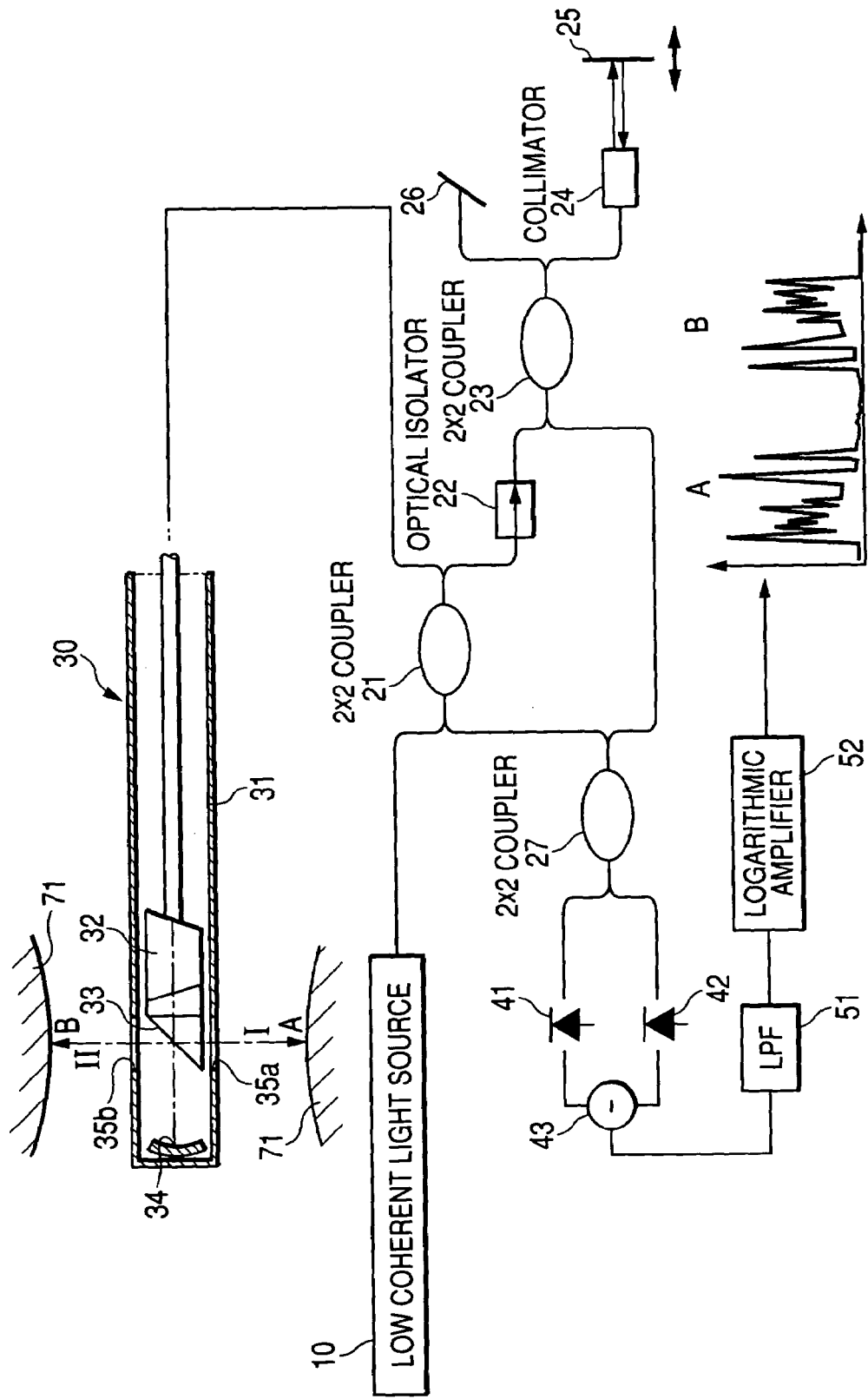
FIG. 1 is an outline view showing an optical tomographic apparatus according to a first exemplary embodiment of the invention.

FIG. 1 is an outline view showing an optical tomographic apparatus according to a first exemplary embodiment of the invention.

The optical tomographic apparatus according to the embodiment is applied to, for example, an endoscope for medical use and mainly includes a light source portion, an interferometer and a signal processing portion.

The light source portion includes a low coherent light source 10. The lower coherent light source 10 is a light source for emitting light having a wide spectrum width (wide wavelength band) in a near infrared region and is preferably constituted by for example, SLD (Super-luminescent diode) or ASE (Amplified Spontaneous Emission) light source or the like.

Further, the interferometer constitutes a Michelson interferometer of a called balance type as a whole and is provided with three 2×2 couplers 21, 23, 27 for dividing and/or combining a light flux(es) guided by an optical fiber (indicated by a black bold line in the drawing) as a waveguide, a probe 30 for acquiring tomographic image information from a subject 71, a reference mirror 25, two optical detectors 41, 42 for detecting image information from the subject 71, and an operator 43.

Further, whereas an optical isolator 22 is arranged at an optical fiber between the 2×2 couplers 21, 23, a collimator 24 is arranged at an optical fiber between the 2×2 coupler 23 and the reference mirror 25. Further, an end portion of other optical fiber connected to the 2×2 coupler 23 is arranged with an attenuator 26 functioning as a nonreflecting terminal end. Further, the reference mirror 25 is made to be movable in an optical axis direction (refer to an arrow mark of FIG. 1) by a publicly known/well known movement controlling means, not illustrated.

The signal processing portion is provided with a low pass filter (LPF) 51 and a logarithmic amplifying portion 52.

Explaining here of a constitution of the probe 30, according to the probe 30, as shown by FIG. 1, inside of a flexible sheath 31 is contained with a GRIN lens 32 as an object optical system, a semitransparent mirror (actually, including a right angle prism provided with a semitransparent mirror at an inclined face thereof; same as follows) 33 and a concave mirror 34 along with an optical fiber. Further, although a flat face mirror can be arranged in place of the concave mirror 34, it is preferable to use the concave mirror 34 in view of capable of making a beam profile excellent.

That is, a fore-end portion (a front end portion) of the sheath is formed in a closed state, and at an inner portion at a vicinity of the fore-end portion, a concave portion of the concave mirror 34 is arranged to face a direction opposed to the fore-end portion of the sheath 31. Further, actually, a portion of being arranged with the semitransparent mirror 33 and the concave mirror 34 is constituted by a member in a shape of a hollow cylinder integrally formed with the sheath 31 by using a comparatively rigid member different from a flexible member forming the sheath 31 to achieve a function of protecting the GRIN lens 32, the semitransparent 33 and the concave mirror 34. Further, in FIG. 1, a detailed illustration of the portion is omitted to facilitate understanding by simplifying the explanation.

On the other hand, an optical fiber is inserted from other end side of the sheath 31, a fore-end portion thereof is contained and arranged to be disposed at a portion spaced apart from the concave mirror 34 by a distance therebetween, and the fore-end portion is arranged with the GRIN lens as the object optical system and the semitransparent mirror 33 successively to the fore-end side of the sheath 31. Further, it is preferable to arrange the semitransparent mirror 33 and the concave mirror 34 and the GRIN lens 32 such that respective centers of the semitransparent mirror 33 and the concave mirror 34 coincide with an optical axis of the GRIN lens 32.

Further, the sheath 31 is formed with light transmitting window portions 35$a$, 35$b$ in a peripheral direction at a vicinity at which the semitransparent mirror 33 is disposed. That is, the light transmitting window portions 35$a$, 35$b$ are formed at two portions spaced apart from each other by an angle of 180 degrees in the peripheral direction of the sheath 31. This is for enabling two fluxes of light having advancing directions different from each other by 180 degrees to be emitted from the probe 30 and enabling to acquire fluxes of back scattered light generated by irradiating the respective fluxes of light to the subject 71 to return to the probe 30 by using the semitransparent mirror 33 as described later in details.

Next, total operation of the embodiment apparatus will be explained.

When low coherent light is emitted from the low coherent light source 10, emitted light is transmitted to the 2×2 coupler 21 by an optical fiber, divided in two of a first light flux and a second light flux by the 2×2 coupler 21, and whereas the first light flux is transmitted to the probe 30 by the optical fiber, the second light flux is transmitted to the 2×2 coupler 23 by way of the optical isolator 22 by other optical fiber.

The first light flux transmitted to the probe 30 is guided to the GRIN lens 32 and is incident on the semitransparent mirror 33 by way of the GRIN lens 32. The first light flux incident on the semitransparent mirror 33 transmits through the semitransparent mirror 33 and is divided in two of light advancing in a direction of the fore-end of the probe 30 along the optical axis of the GRIN lens 32 and light reflected in a direction orthogonal to the optical axis of the GRIN lens 32 at the semitransparent mirror 33.

Light reflected in the direction (refer to an arrow mark I of FIG. 1) orthogonal to the optical axis of the GRIN lens 32 by the semitransparent mirror 33 is irradiated to the subject 71 outside of the probe 30 by passing through the light transmitting window portion 34$a$.

On the other hand, light advancing in the direction of the fore-end of the probe 30 by transmitting through the semitransparent mirror 33 is incident on the concave mirror 34, reflected thereby to advance inversely through an incident path to the concave mirror 34, is incident on the semitransparent mirror 33, reflected in a direction (refer to an arrow mark II of FIG. 1) inverse to preceding light reflected without passing through the semitransparent mirror 33 precisely by 180 degrees, and irradiated to the subject 71 by passing through the light transmitting window portion 35$b$. Further, for convenience of the explanation, notation A is attached to a portion of the subject 71 irradiated by light from an optical path indicated by the arrow mark I and notation B is attached to a portion of the subject 71 irradiated with light from an optical path indicated by the arrow mark II, respectively. Further, in order to facilitate understanding, distances between the probe 30 and portions A, B of the subject 71 are made to be substantially equal.

Therefore, light on one side irradiated to the subject 71 by the optical path indicated by the arrow mark I in FIG. 1 and light on other side irradiated to the subject 71 by the optical path indicated by the arrow mark II in FIG. 1 are irradiated to the subject 71 by an optical path difference twice as much as a distance between the semitransparent mirror 33 and the concave mirror 34.

Light irradiated to the subject 71 in this way advances to an inner portion of the subject 71 to generate back scattered light at respective tomographic boundary portions at which a refractive index distribution mainly becomes discontinuous. Respective fluxes of back scattered light generated at the respective tomographic boundary portions in a depth direction of the subject 71 are provided with slight coherence, the respective fluxes advance inversely through an irradiation path as subject light while being accompanied by light delay amounts in accordance with a depth direction and incident on the semitransparent mirror 33 by passing through the light transmitting window portions 35a, 35b of the probe 30.

Here, subject light (object light) returning from the portion A of the subject 71 by the optical path indicated by the arrow mark I of FIG. 1 is incident on the semitransparent mirror 33, reflected by right angle in the direction of the GRIN lens 32 to be substantially along the optical axis, advances inversely through the path in advancing from the low coherent light source 10 to reach the 2×2 coupler 21 and is transmitted to the 2×2 coupler 27 by way of an optical fiber. On the other hand, subject light returning form the portion B of the subject 71 by the optical path indicated by the arrow mark II of FIG. 1 is incident on the semitransparent mirror 33, reflected in the direction of the concave mirror 34, reflected in a direction inverse to the incident path by the concave mirror 34 to transmit through the semitransparent mirror 33 and the GRIN lens 32 and transmitted to the 2×2 coupler 27 similar to subject light tracking the optical path indicated by the arrow mark I.

On the other hand, the second light flux precedingly transmitted to the 2×2 coupler 23 is irradiated to the reference mirror 25 by way of the collimator 24, reflected in a direction inverse to an incident direction at a reflecting face thereof, advances inversely through the incident path as reference light to reach again the 2×2 coupler 23 by way of the collimator 24 and is transmitted to the 2×2 coupler 27 by the optical fiber.

Subject light and reference light transmitted to the 2×2 coupler 27 is combined together by the 2×2 coupler 27, the two combined waves are provided with extremely short coherence lengths and therefore, the two waves interfere with each other only when light delay amounts (optical path lengths) of the respectives are substantially equal. Therefore, there is provided interference information only at a position in the depth direction of the subject 7 in correspondence with a position in an optical axis direction of the reference mirror 25 (coinciding with a direction of scanning the reference mirror 25 indicated by an arrow mark of FIG. 1) and therefore, by moving the reference mirror 25 in the optical axis direction, interference wave information at respective positions in the depth direction of the subject 71 is time-sequentially provided.

Here, as described above, there are fluxes of subject light from the subject 71 from portion A of the subject 71 and portion B of the subject, the fluxes reach the 2×2 coupler 27 successively by a time difference in accordance with the optical path difference in the probe 30 explained above and respectively combined with fluxes of reference light. Further, with regard to respectives of portions A, B of the subject 71, interference information of respective positions in the depth direction is time-sequentially provided as described above.

Thereafter, interference light provided by the 2×2 coupler 27 is subjected to a balance detecting processing using two optical detectors 41, 42 and the operator 43. That is, respective signals outputted from the optical detectors 41, 42 are inputted to the operator 43 to calculate a difference between the two signals to output a difference signal canceling a noise component and a drift component.

The difference signal from the operator 43 is removed of an unnecessary high frequency component by the low pass filter 51 and thereafter, logarithmically amplified by the logarithmic amplifier 52 and outputted with a time difference in accordance with the above-described optical path difference at the probe 30, mentioned above, as a one-dimensional tomographic image signal with regard to portion A of the subject 71 and a one-dimensional tomographic image signal with regard to portion B of the subject 71 (refer to signal waveforms A, B shown in FIG. 1).

According to the optical tomographic apparatus of the first embodiment, by pivoting the probe 30 by 180 degrees, tomographic image information in the peripheral direction of the subject 71 can be provided and therefore, an information acquiring speed twice as much that of the related art apparatus is realized. Further, when the probe 30 is pivoted by 360 degrees, an information amount twice as much as that in the related art can be acquired in the peripheral direction of the subject 71.

Further, in the above-described first embodiment, there may be constructed a constitution of using circulators for the 2×2 couplers 21, 23, 27. Further, although according to the first embodiment, the semitransparent mirror 33 may be fixedly provided at inside of the probe 30 and the probe 30 per se may be pivoted, further preferably, there may be constructed a constitution in which the semitransparent mirror 33 can freely be pivoted by providing a pivoting mechanism constituting a rotating axis by the optical axis of the GRIN lens 32 as mentioned later.

Figure 2:
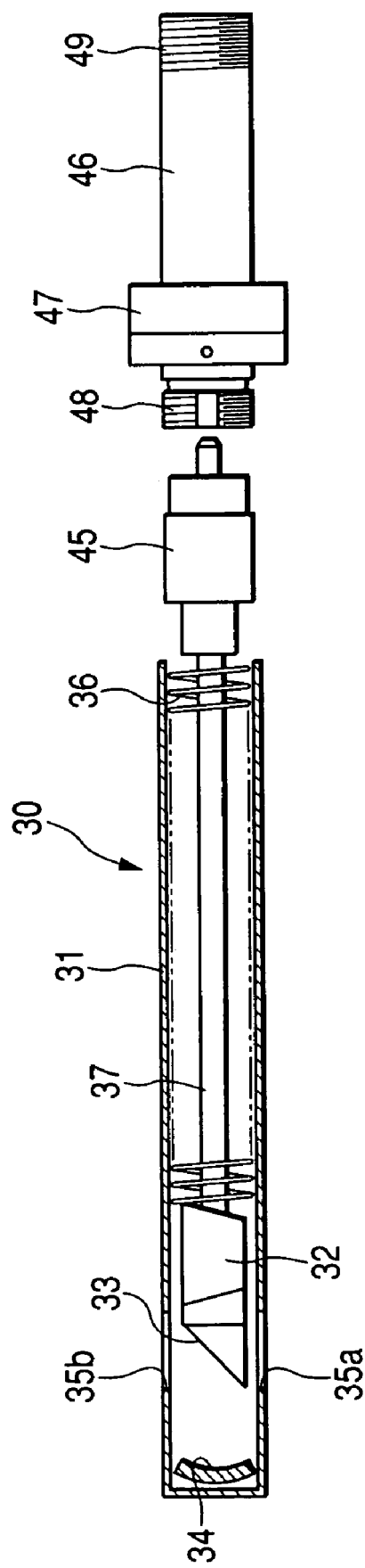
FIG. 2 is an outline sectional view showing a constitution when a probe is provided with a pivoting mechanism.

FIG. 2 shows a constitution example of a pivoting mechanism for pivoting the semitransparent mirror 33 and the pivoting mechanism will be explained in reference to the drawing as follows.

According to the constitution example, inside of the sheath 30 is contained with a spiral spring 36 in series up to a base end side of the sheath 30 to be brought into contact with a portion of the GRIN lens 32 on a side opposed to a portion thereof at which the semitransparent mirror 33 is disposed and the GRIN lens 32 and the semitransparent mirror 33 are integrated along with a fiber bundle 37 and is made to be rotatable centering on the optical axis of the GRIN lens 32.

That is, the fiber bundle 37 is connected to a plug 45 fixedly attached to the base end portion of the sheath 30 and the plug 45 is attached with a rotation operating portion 46 by being screwed to a receptacle 48 formed at the rotation operating portion 46.

The rotation operating portion 46 is formed with receptacles 48, 49 at both end portions thereof and is provided with an operation ring 47 at an outer peripheral portion thereof. Further, whereas the receptacle 48 on the front end side is connected to the plug 45 provided at the base end portion of the sheath 30 as described above, the other receptacle 49 is connected to the 2×2 coupler 21 by way of the optical fiber. Further, by pivoting the operation ring 47, the spiral spring 36, the fiber bundle 37, the GRIN lens 32 and the semitransparent mirror 33 can integrally be pivoted centering on the optical axis of the GRIN lens 32. Further, in this case, a plurality of the transmitting window portions 35a, 35b may be formed in the peripheral direction, or the transmitting window portions 35a, 35b may continuously be formed to enable light to come and go from and to an arbitrary portion in the peripheral direction of the probe 30 in accordance with pivoting the semitransparent mirror 33.

Figure 3:
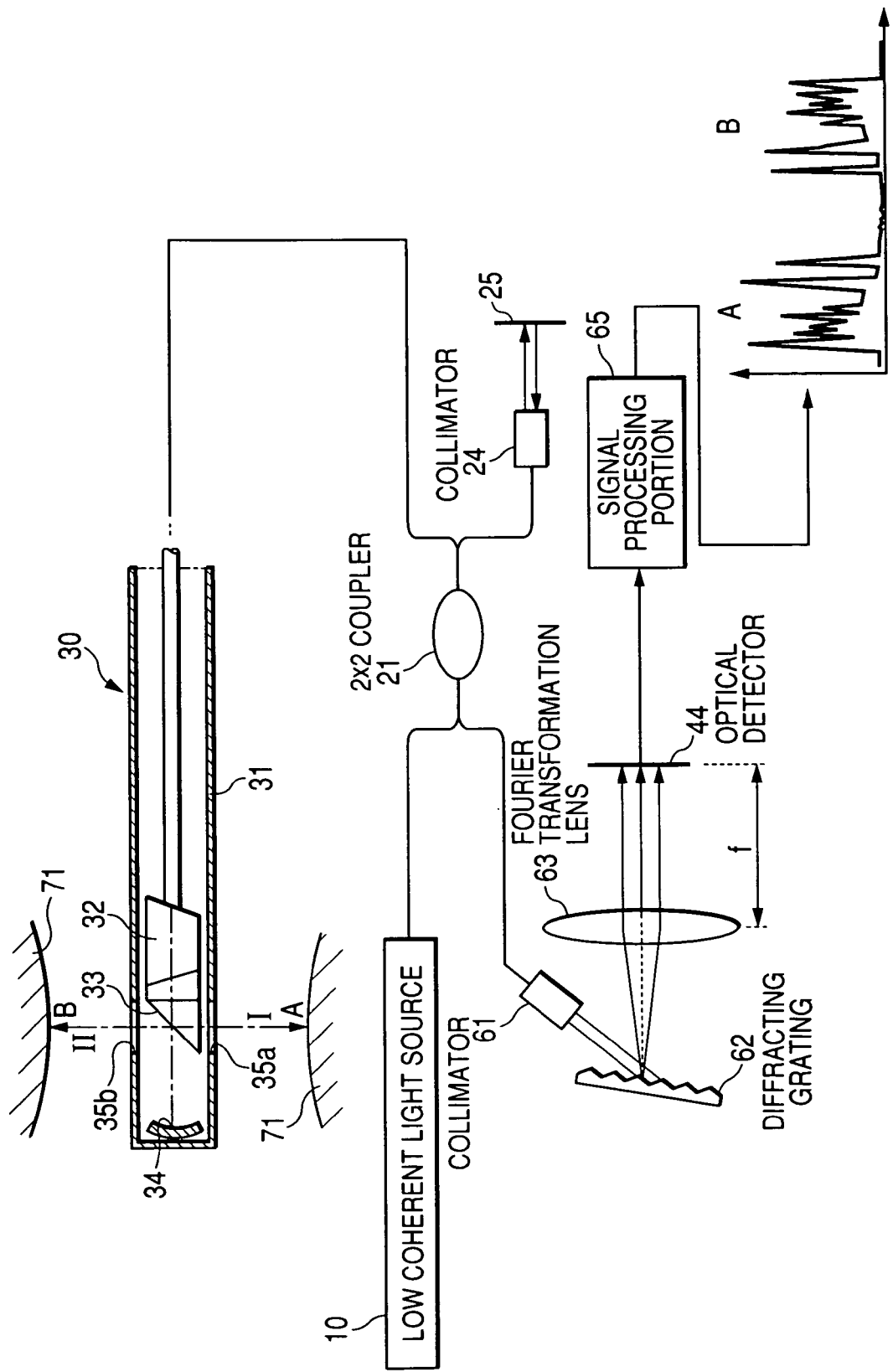
FIG. 3 is an outline view showing an optical tomographic apparatus according to a second exemplary embodiment of the invention.

Next, an explanation will be given of an optical tomographic apparatus according to a second exemplary embodiment of the invention in reference to FIG. 3. Further, constituent elements the same of those of the optical tomographic apparatus according to the above-described first embodiment are attached with the same notations and a detailed explanation thereof will be omitted and in the following, an explanation will be given centering on a different point as follows.

The optical tomographic apparatus according to the second embodiment differs from the optical tomographic apparatus according to the first embodiment in that an interference light flux is inputted to an optical detector by way of a spectroscopic optical system.

That is, first, although that the 2×2 coupler 21 is connected with the low coherence light source 10 and connected with the probe 30 is similar to that in the optical tomographic apparatus according to the first embodiment, that the collimator 24 and a collimator 61 constituting an element of constituting a spectroscopic optical system (details of which will be described later) are connected thereto respectively by way of separate optical fibers differs from that in the case of the first embodiment. Further, the reference mirror 25 is arranged to be spaced apart from the collimator 24 by a pertinent distance therebetween. Further, according to the embodiment, the reference mirror 25 is fixed to a predetermined position.

Therefore, at the 2×2 coupler 21, subject light and reference light from the reference mirror 25 are combined and so-called interference light is transmitted to the collimator 61 of the spectroscopic optical system.

The spectroscopic optical system includes the collimator 61, a diffraction grating 62 and a Fourier transformation lens 63. In the spectroscopic optical system, interference light transmitted from the 2×2 coupler 21 to the collimator 61 by way of an optical fiber is made to be parallel light by the collimator 61 and is irradiated to the diffraction grating 62 of a reflection type.

The diffraction grating 62 is provided at a front side focal position of the Fourier transformation lens 63, diffraction light from the diffraction grating 62 transmits through the Fourier transformation lens 63 and is irradiated to an optical detector 44 provided at a position of being remote from the Fourier transformation lens 63 by a focal distance f. The optical detector 44 is preferably, for example, a so-to-speak linear image sensor or the like.

Here, by subjecting diffraction light from the diffraction grating 62 to Fourier transformation operation by the Fourier transformation lens 63, interference spectrum in accordance with interference of light waves of subject light and reference light is formed on the optical detector 44. That is, in other words, a combined power spectrum of subject light and reference light is incident on the optical detector 44.

An output of the optical detector 44 is inputted to a signal processing portion 65, by the signal processing portion 65, the output is subjected to a signal processing necessary for providing a one-dimensional tomographic image signal reflected with information in the depth direction of the subject 71 and the tomographic image signal with regard to a portion of the subject 71 irradiated with low coherent light is provided from the signal processing portion 65. Further, by subjecting the tomographic image signal provided in this way to a processing necessary for forming an image at a publicly-known/ well known image processing portion, not illustrated, a tomographic image can be displayed on a display apparatus, not illustrated.

Next, total operation of the optical tomographic apparatus according to the second embodiment will be explained.

First, low coherent light from the low coherent light source 10 is divided in two of a light flux irradiated to the reference mirror 25 by way of the 2×2 coupler 21 and a light flux irradiated to the subject 71 by way of the probe 30, further, that the light flux advancing to the probe 30 is irradiated to two portions A, B of the subject 71 by a predetermined optical path difference therebetween is basically similar to that in the case of the first embodiment. Further, distances between the probe 30 and portion A and portion B of the subject 71 are made to be substantially equal similar to the previous first embodiment.

Further, subject light from the subject 71 returns again to the 2×2 coupler 21 by way of the probe 30, combined with reference light reflected by the reference mirror 25 at the 2×2 coupler 21 and is transmitted to the collimator 61 by way of the optical fiber as interference light.

Interference light transmitted to the collimator 61 is made to be parallel light thereby and is irradiated to the diffraction grating 62. Interference light incident on the diffraction grating 62 is dispersed in a wavelength and is reflected to the Fourier transformation lens 63. Further, reflected light from the diffraction grating 62 is subjected to Fourier transformation operation by transmitting through the Fourier transformation lens 63 and irradiated to the optical detector 44.

Light incident on the optical converter 44 is photoelectrically converted into optical intensity signals (spectrum interference fringes) for respective spectra. Further, at the signal processing portion 65, there is carried out a signal processing necessary for providing a one-dimensional tomographic image signal reflected with information in the depth direction of the subject 71, as a result, as shown by FIG. 3, tomographic image signals in correspondence with portions A, B at two portions of the subject 71 are provided in a state of being separated from each other (refer to A, B in a signal waveform diagram of FIG. 3). Further, the respective image signals in correspondence with portions A, B of the subject 71 are separately provided owing to the optical path difference in irradiating low coherent light respectively to portions A and portion B of the subject 71 similar to the previous first embodiment.

Further, although in the probe 30 according to the second embodiment, similar to the case of the first embodiment, the semitransparent mirror 33 is fixedly provided at inside of the probe 30, the invention needs not to be limited to such a constitution but there may naturally be constituted a structure of capable of pivoting the semitransparent mirror 33 by the pivoting mechanism explained in reference to FIG. 2. In this case, as described above, a plurality of the light transmitting window portions 35a, 35b may be provided in the peripheral direction, or the light transmitting window portions 35a, 35b may continuously be formed.

Further, according to the second embodiment, there may be constructed a constitution of substituting a circulator for the 2×2 coupler 21.

Further, in the above-described embodiment, with regard to portion A and portion B of the subject 71, there is provided an optical path length difference in correspondence with twice as much as the distance between the semitransparent mirror 33 and the concave mirror 34 between fluxes of irradiating light for irradiating portion A and portion B respectively to provide the tomographic image signals A, B separated from each other, it is preferable to predict ranges of the respective distances previously from the semitransparent mirror 33 to portion A and portion B and adjust a distance between the semitransparent mirror 33 and the concave mirror 34 such that an optical path length difference of a predetermined value or more is necessarily produced between the two fluxes of irradiated light within the ranges.

However, the constitution of making the above-described two tomographic image signals A, B separable from each other is not limited thereto. For example, with regard to the two fluxes of irradiating light, there may be constructed a constitution in which wavelengths thereof differ significantly from each other, or polarized components thereof significantly differ from each other to make the tomographic image signals A, B provided finally separable from each other.

Figure 4:
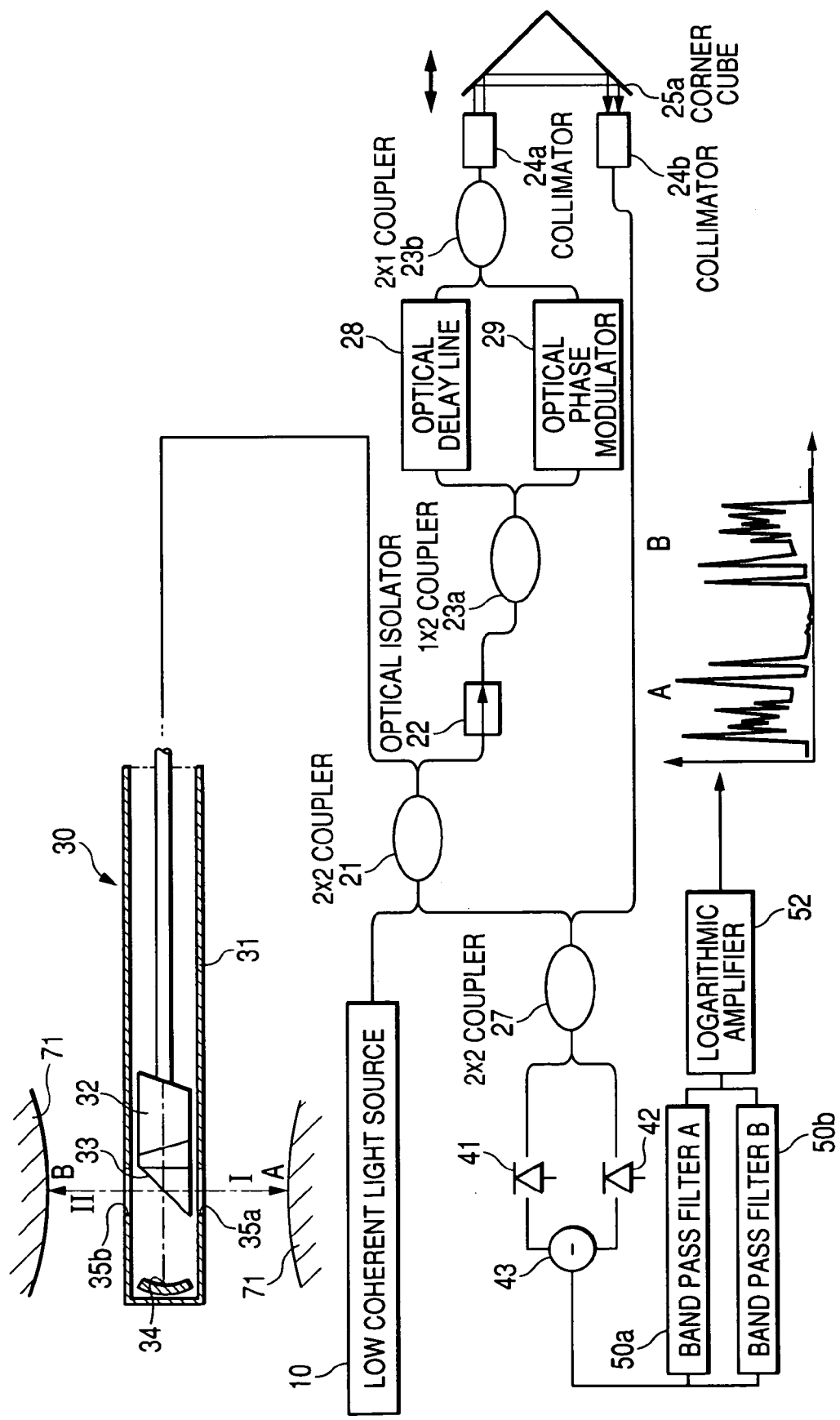
FIG. 4 is an outline view showing an optical tomographic apparatus according to a third exemplary embodiment of the invention.

FIG. 4 shows an exemplary embodiment (third embodiment) when the above-described wavelengths are made to differ from each other. In an optical tomographic apparatus according to the third embodiment, constituent elements the same as those of the optical tomographic apparatus according to the above-described first embodiment are attached with the same notations and a detailed explanation thereof will be omitted, and in the following, an explanation will be given only of a different point.

That is, at a poststage of the optical isolator 22, there are provided two 1×2 couplers 23a, 23b, an optical delay line 28 and an optical phase modulator 29 arranged in parallel between the two 1×2 couplers 23a, 23b, a collimator 24a, a corner cube 24a, and a collimator 24b arranged at a poststage of the 1×2 coupler 23b, further, a band pass filter A 50a for a first wavelength band (for example, wavelength band centering on a wavelength λ1) as well as a band pass filter B 50b for a second wavelength band (for example, wavelength band centering on a wavelength λ2: for example, λ1>λ2) which does not overlap the first wavelength band are provided in place of the low pass filter 51 according to the first embodiment. The corner cube 25a is made to be movable in a direction of inputting and emitting light, and an optical path length of reference light is made to be able to be changed thereby.

Also according to the third embodiment, the signal in correspondence with portion A of the subject 71 and the signal in correspondence with portion A of the subject 71 are separately provided, the signal in correspondence with portion A of the subject 71 is provided from a signal passing through the optical delay line 28 and the band pass filter A 50a, on the other hand, the signal in correspondence with portion B of the subject 71 is provided from a signal passing through the optical phase modulator 29 and the band pass filter B 50b. That is, the signal in correspondence with portion A is constituted only by information by the wavelength band passing through the band pass filter A 50a, on the other hand, the signal in correspondence with portion B is constituted only by information by the second wavelength band passing through the band pass filter B 50b, and even when the two signals overlap each other over time, pieces of information carried by signals can excellently be separated in accordance with a difference between the wavelengths. In other words, the optical delay line 28 functions to make the both signal overlap each other over time. Further, the optical phase modulator 29 is provided with a function of promoting S/N ratio in correspondence with portion B.

After the signals are separated from each other in accordance with the difference between the wavelengths in this way, the signals may be displayed separately as shown by FIG. 4 in order to make the respective tomographic image signals in correspondence with portions A, B of the subject 71 optically recognizable.

Further, in any of the above-described embodiments, the subject is not limited to the human body but can be other various tissues providing reflected light from respective positions at inner portions thereof by advancing light to the inner portions.

While the invention has been described in detail and with reference to specific embodiments thereof, it will be apparent to one skilled in the art that various changes and modifications can be made therein without departing from the spirit and scope thereof.

The present application claims foreign priority based on Japanese Patent Application No. JP2004-356137 filed Dec. 9, 2004, the contents of which is incorporated herein by reference.

What is claimed is:

1. An optical tomographic apparatus capable of providing a tomographic image of a subject, which comprises:
   a probe comprising: a reflecting mirror; a semitransparent mirror; and an object optical system in this order from a side of a fore-end portion of the probe;
   a light source that emits light having low coherence; and
   an interferometer that: divides the light emitted from the light source into two lights; irradiates the subject with one of the two lights; irradiates a reference face with the other of the two lights; combines reference light reflected from the reference face and subject light reflected from the subject so as to obtain interference light; and photoelectrically converts the interference light into a signal so as to enable to output the signal,
   wherein the interferometer comprises said probe that emits irradiating light to the subject and receives the subject light reflected from the subject, and the semitransparent mirror of the probe that separates the irradiating light into first irradiating light and second irradiating light, the first irradiating light is reflected by the semitransparent mirror so that the probe emits the first irradiating light in a first side direction of the probe and the second irradiating light transmits through the semitransparent mirror to the reflecting mirror, is reflected by the reflecting mirror to return again to the semitransparent mirror, and is reflected by the semitransparent mirror so that the probe emits the second irradiating light in a second side direction of the probe, the second side direction being a direction inverse to the first side direction.

2. The optical tomographic apparatus according to claim 1, wherein the reflecting mirror is a concave mirror having a concave surface facing to the semitransparent mirror.

3. The optical tomographic apparatus according to claim 1, wherein the probe comprises a pivoting mechanism capable of rotating the semitransparent minor on an optical axis of the object optical system.

4. The optical tomographic apparatus according to claim 1, wherein the interferometer comprises a Michelson interferometer comprising a reflecting member, the reflecting member having the reference face, and an optical length of the reference light is changed by moving the reflecting member in a direction along an optical axis of the reflecting member.

5. The optical tomographic apparatus according to claim 1, wherein the interferometer comprises: a Michelson interferometer; an optical detector; and a spectroscopic optical system that separates the interference light, and the interference light is guided to the optical detector by way of the spectroscopic optical system.

6. The optical tomographic imaging apparatus according to claim 1, which comprises: a light delaying unit; an optical phase-modulating unit; and two band pass filters having passing wavelength bands different from each other, wherein the reference light is provided by inputting and passing the light irradiated to the reference face through the light delaying unit and the optical-modulating unit in parallel, and the interference light provided by combining the reference light and the irradiating light is photoelectrically converted and is separated by the two band pass filters so as to provide first and second optical tomographic image information corresponding to the first and the second irradiating light, respectively.

7. An optical tomographic apparatus capable of providing a tomographic image of a subject, which comprises:

a light source that emits light having low coherence, an interferometer that: divides the light emitted from the light source into two lights; irradiates the subject with one of the two lights; irradiates a reference face with the other of the two lights; combines reference light reflected from the reference face and subject light reflected from the subject so as to obtain interference light; and photoelectrically converts the interference light into a signal so as to enable to output the signal, wherein the interferometer comprises a probe that emits irradiating light to the subject and receives the subject light reflected from the subject, and the probe comprises an irradiating light-separating unit that separates the irradiating light into first irradiating light and second irradiating light, the probe emitting the first irradiating light in one side direction of the probe and the second irradiating light in another side direction of the probe, a light delaying unit; an optical phase-modulating unit; and two band pass filters having passing wavelength bands different from each other, wherein the reference light is provided by inputting and passing the light irradiated to the reference face though the light delaying unit and the optical-modulating unit in parallel, and the interference light provided by combining the reference light and the irradiating light is photoelectrically converted and is separated by the two band pass filters so as to provide first and second optical tomographic image information corresponding to the first and the second irradiating light, respectively.

* * * * *